United States Patent [19]

Olson

[11] Patent Number: 5,011,475

[45] Date of Patent: Apr. 30, 1991

[54] PROTECTOR FOR INTRAVENOUS AND SYRINGE NEEDLES

[76] Inventor: Richard A. Olson, 210 W. Grant #122, Minneapolis, Minn. 55403

[21] Appl. No.: 360,770

[22] Filed: Jun. 2, 1989

[51] Int. Cl.$^5$ .............................................. A61M 5/32
[52] U.S. Cl. ...................................... 604/192; 604/263
[58] Field of Search ................ 604/192, 263, 197, 198

[56] References Cited

U.S. PATENT DOCUMENTS

| | | | |
|---|---|---|---|
| 4,681,567 | 7/1987 | Masters et al. | 604/198 |
| 4,838,871 | 6/1989 | Luther | 604/192 |
| 4,840,619 | 6/1989 | Hughes | 604/192 |

Primary Examiner—Stephen C. Pellegrino
Assistant Examiner—Ralph A. Lewis
Attorney, Agent, or Firm—John W. Adams

[57] ABSTRACT

This invention includes an external protective sheath for normally enclosing a medical needle to provide a safety protective enclosure normally surrounding the needle, but being adapted to be temporarily removed from needle enclosing protective position to expose the needle for use in penetrating a patient's blood vessel for injection of medication from a syringe or for introduction of intravenous tubing and said sheath being moveable back into protective position around the needle after use.

3 Claims, 2 Drawing Sheets

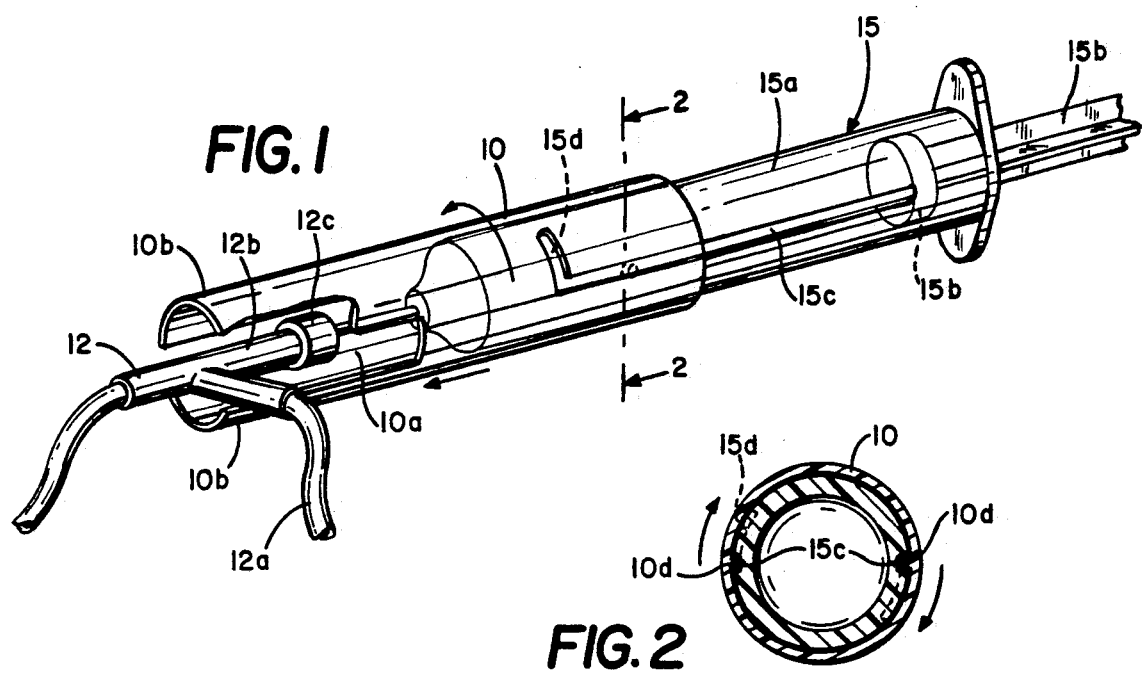
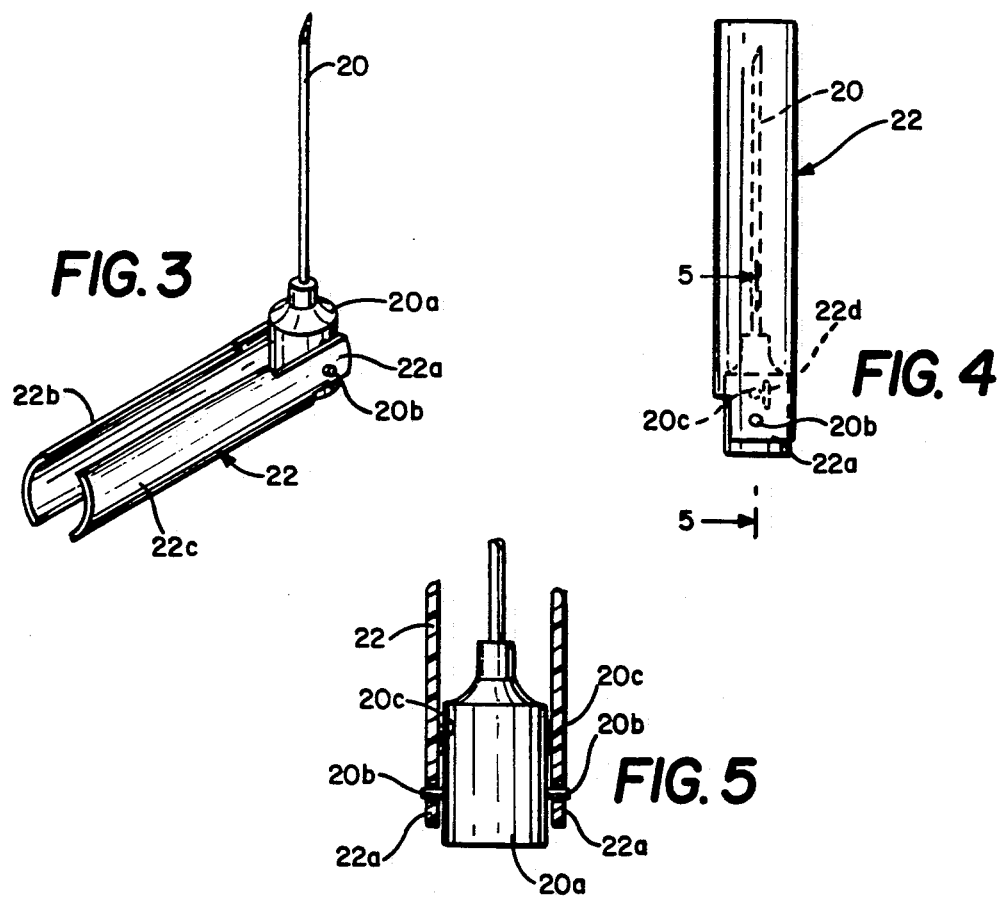

PROTECTOR FOR INTRAVENOUS AND SYRINGE NEEDLES

BACKGROUND OF THE INVENTION

It has long been a problem to protect medical personnel from being stuck or scratched by a needle after use. The problem has become increasingly serious with the spread of the AIDS virus through contamination of a needle after use on a patient having AIDS. After withdrawal of the needle from the infected patient, a scratch on the hand or arm of the medical person using the needle would expose that medical person to the AIDS virus.

SUMMARY OF THE INVENTION

This invention provides an external protective sheath which normally encloses a medical needle but which may be temporarily removed from needle-enclosing protective position to expose the needle for use to withdraw medication from a vial for injection into a patient or into intravenous tubing. The protective sheath may be quickly and easily repositioned after use to enclose the needle and prevent the same from striking and penetrating the skin of the person administering the injection or other medical personnel in attendance.

DETAILED DESCRIPTION OF THE DRAWINGS

FIG. 1 is a perspective view showing one form of the invention;

FIG. 2 is a sectional view taken substantially along line 2—2 of FIG. 1;

Figure 6:
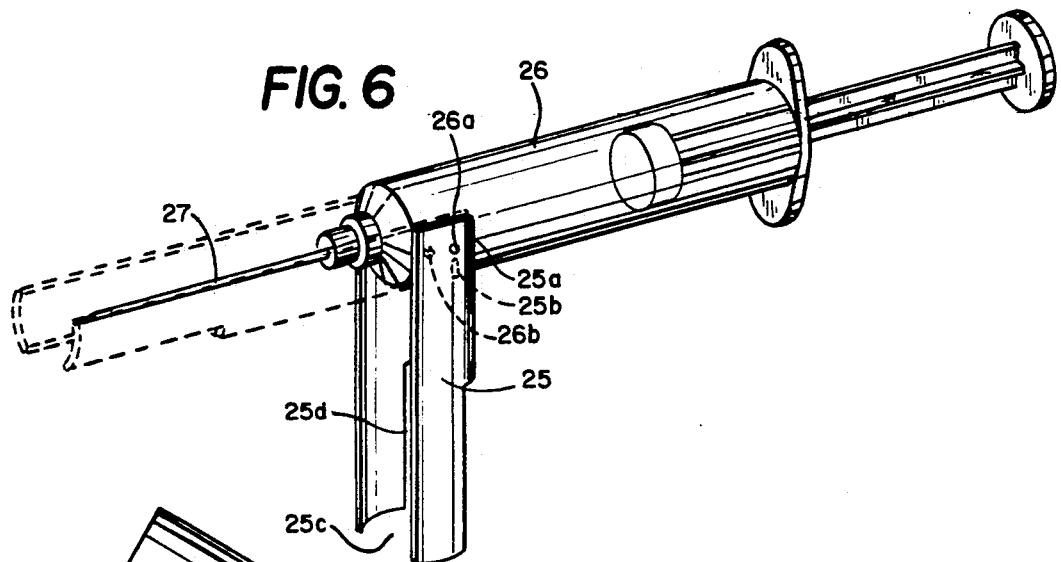

FIGS. 3, 4, and 5 show another form of the invention;

FIG. 6 shows another modification; and

Figure 7:
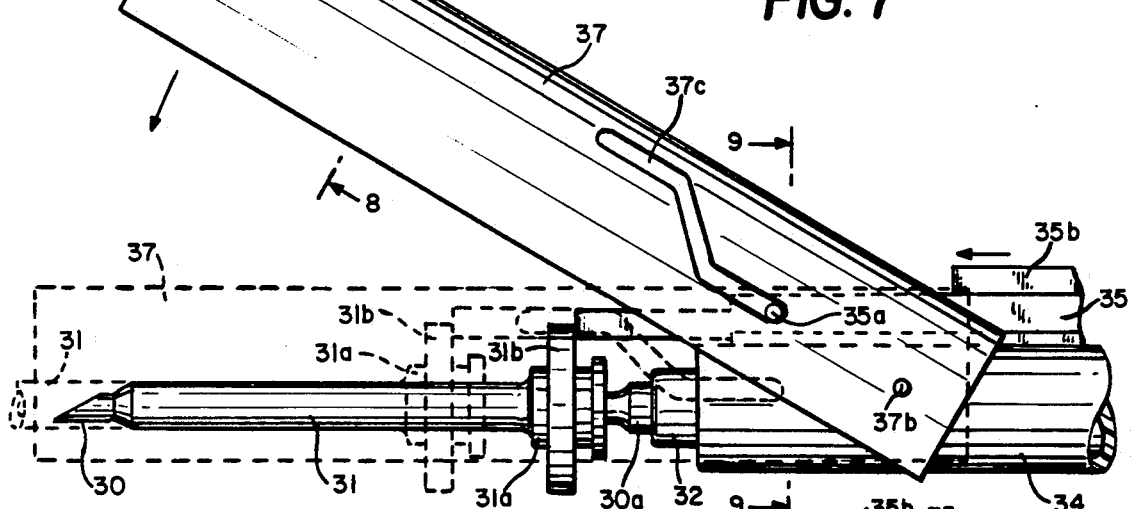
Figure 8:
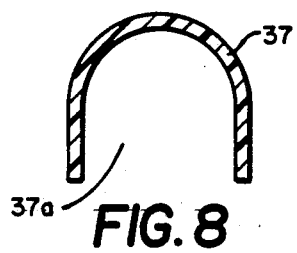
Figure 9:
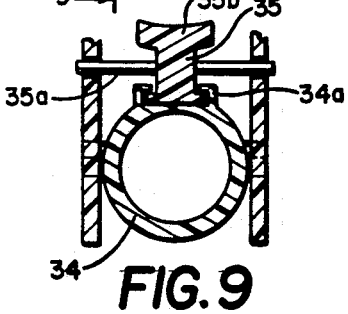

FIGS. 7, 8, and 9 show still another modification of the invention.

DETAILED DESCRIPTION OF THE PREFERRED EMBODIMENT

FIGS. 1 and 2 illustrate one form of the invention. In this form the sheath member 10 is in the form of a cylindrical sleeve having cut-out slots 10a in the forward end thereof to form a pair of sheath elements 10b on both sides of the slots 10a.

An intravenous (IV) tube 12 is illustrated having a main supply tube 12a and a branch tube 12b. The supply tube 12a may be received in one of the cut out slots 10a between the two sheath elements 10b as shown in FIG. 1 when an injection is made into the branch tube 12b. A conventional sealing cap 12c normally closes the end of the branch tube 12b.

The cylindrical body of the sheath 10 is slidably mounted on the outside of a conventional syringe 15 which has a tubular body portion 15a and a plunger unit 15b slidably mounted within the body. The tubular body portion 15a forms a mounting hub for the sheath 10. The outside of the body 15a is provided with grooves 15c and the cylindrical mounting portion of the sheath 10 is provided with knobs 10d on the inside thereof. The inwardly extending knobs 10d are received in the respective grooves 15c for sliding engagement therein to permit the sheath 10 to be retracted to expose substantially the full length of the syringe needle for use. The cut out slots 10a are wide enough to receive the supply tube 12a so that the sheath 10 will not interfere with a syringe injection into the branch tube 12b. The grooves 15c are provided with circumferentially extending locking portions 15d so that when the sheath 10 is in fully extended maximum protection position, the knobs 10d will be shifted to the forward ends of the groove portions 15c. In this position the cylindrical sheath portion 10 may be rotated to seat the knobs 10d against the closed ends of the circumferential slot portions 10d. In this form of the invention it will be seen that the protective sheath assembly is mounted on the injection syringe 15 to work in conjunction therein.

FIGS. 3, 4, and 5 show a modified form of the invention wherein a sheath 22 is mounted on a needle unit 20. The needle 20 has a hub portion 20a adapted to be connected to the discharge end of an IV tube or to the discharge end of a syringe (not shown). The sheath 22 is provided with a pair of spaced attachment arms 22a which are pivotally connected to opposite sides of the hub 20a as by pivot pins 20b mounted on said hub and extending through registered apertures in the arms 22a. The protective end portion side of sheath 22 has generally U-shaped cross section with an open side 22b extending the full length thereof. An elongated slot 22c extends longitudinally through a major portion of the opposite side of sheath member 22 to permit usage with an IV tube assembly such as the supply tube 12a and branch tube 12b (shown in FIG. 1). The slot 22c permits the needle 20 to be inserted through the IV cap 12c without retraction of the sheath 22. The longitudinal openings 22b and 22c of the sheath 22 are only sufficiently wide to permit the sheath to remain in protective position, while the needle is inserted into the IV branch tube 12b, and prevent the finger of an operator from contacting the needle. Means are provided for releasably holding the needle in aligned protective position as shown in FIGS. 4 and 5, such as suitable retaining knobs 20c provided on the outside of the needle hub 20a and a pair of stop bars or projections 22d provided on the inside of the arms 22a. The knobs 20c engage the stop bars 22d to positively maintain the sheath 22 in aligned protective position surrounding over the needle 20.

FIG. 6 shows a form of the invention which is somewhat similar to the form of the invention shown in FIGS. 1 and 2 except that the sheath 25 is pivotally mounted on the outside of a syringe tube 26 which has a needle 27 attached thereto. The syringe tube has a pair of pivot pins 26a attached thereto near the discharge end thereof to pivotally connect the bifurcated attachment arms 25a of the sheath 25 to the syringe 26. A pair of stop pins 26b are also formed on the outside of the syringe 26 in spaced relation to the pins 26a and stop ribs 25b on arms 25a frictionally engage the surface of the syringe 26 and abut the pins 26a. The protector sheath 25 is also provided with an open end 25c and an elongated access slot 25d to facilitate use with an IV branch tube arrangement such as previously described.

FIGS. 7, 8, and 9 illustrate a needle protective sheath assembly adapted for use in the installation of an IV catheter into a patient's blood vessel. The pointed inserting end of a needle 30 is illustrated in FIG. 7. The needle 30 is surrounded by a catheter 31 of an IV tube. The catheter 31 has a connecting hub 31a and slidably receives the needle 30 therethrough for initial insertion of the catheter 31 into the patient's blood vessel. The needle 30 has a connecting hub 30a on the rear end thereof connected to a spindle 32 which is fixed to a mounting cylinder 34. The mounting cylinder 34 is provided with a track 34a along the top side thereof and a positioning slide 35 is slidably mounted in said track as illustrated in FIGS. 7 and 9.

A sheath 37 open along one longitudinal side thereof forms an opening 37a as best shown in FIG. 8. The sheath is pivotally mounted on the outside of the mounting cylinder 34 as by pivot pins 37b. A camming pin 35a extends through the upper portion of the slide 35 above the track 34a and is slidably mounted in cam slots 37c formed in the side wall portions of the sheath 37.

To insert the catheter 31 of the IV tube into the patient's blood vessel the sheath is elevated into raised full-line position as shown in FIG. 7 and the needle 30 and catheter 31 are initially inserted into the patient's blood vessel. The catheter 31 has a hub 31a with a collar 31b formed therearound for engagement with the end of slide 35. After initial or partial insertion of the needle and catheter assembly into the blood vessel, the end of the catheter is then projected farther into the blood vessel by pushing forwardly on the finger grip 35b which moves the end of the slide 35 and the collar 31b forwardly. This forward movement of the catheter into the vein may be combined with a rearward retraction of the cylinder 35 which retracts the needle from the catheter to expose the outer end of the catheter hub 31a for a conventional connection to the end of an IV delivery tube. In order to provide a protective covering for the needle after withdrawal, the sheath is automatically lowered into dotted position by the forward movement of on the slide 35. The camming pin 35a travels in the cam slots 37c to produce the lowering of the sheath 37 into protective position around the needle 30.

What is claimed is:

1. A projector assembly for injection needles comprising, a mounting hub, a needle attached to said mounting hub, an elongated hollow protective sheath member mounted on said hub to normally surround the entire needle, and having openings extending longitudinally along both sides thereof to permit the needle to be inserted into one of two conduits of an IV tube assembly in place in a patient's blood vessel, the sheath being pivotally mounted on the mounting hub to permit pivotal retraction of the sheath from the needle on either side thereof to expose the needle for use and permit the sheath to be moved back into protective position around the needle after use and a pair of respectively engageable positioning stop elements respectively mounted on the hub and the sheath for positively positioning the sheath in its desired protective position when said stop elements are engaged.

2. A protector assembly for injection needles comprising, a mounting hub, a needle attached to said mounting hub, an elongated hollow protective sheath member mounted on said hub to normally surround entire needle, and having openings extending longitudinally along both sides thereof to permit the needle to be inserted into one of two conduits of and IV tube assembly in place in a patient's blood vessel, the sheath is pivotally mounted on the mounting hub to permit pivotal retraction of the sheath from the needle to expose the needle for use and permit the sheath to be moved back into protective position around the needle after use, and a slide member mounted for longitudinal movement on the mounting hub axially of the needle and having camming means connected with said sheath and the slide in a manner to cause the sheath to be pivoted upwardly into retracted position when the slide is shifted forwardly and to project the sheath downwardly into protective position when the slide is retracted rearwardly.

3. The structure set forth in claim 2 and said camming means including a pair of camming slots formed in the sheath, and a camming pin mounted on said slide and extending outwardly into the camming slots formed in said sheath to forcibly project the sheath upwardly when the slide is projected forwardly.

* * * * *